United States Patent
Nagakawa et al.

(10) Patent No.: US 7,390,391 B2
(45) Date of Patent: *Jun. 24, 2008

(54) CONCENTRATION MEASURING METHOD, CONCENTRATION TEST INSTRUMENT, AND CONCENTRATION MEASURING APPARATUS

(75) Inventors: Kenji Nagakawa, Kyoto (JP); Hideaki Yamaoka, Kyoto (JP)

(73) Assignee: Arkray, Inc., Kyoto (JP)

( * ) Notice: Subject to any disclaimer, the term of this patent is extended or adjusted under 35 U.S.C. 154(b) by 62 days.

This patent is subject to a terminal disclaimer.

(21) Appl. No.: 10/489,488

(22) PCT Filed: Aug. 30, 2002

(86) PCT No.: PCT/JP02/08855

§ 371 (c)(1), (2), (4) Date: Mar. 12, 2004

(87) PCT Pub. No.: WO03/025558

PCT Pub. Date: Mar. 27, 2003

(65) Prior Publication Data

US 2004/0245121 A1 Dec. 9, 2004

(30) Foreign Application Priority Data

Sep. 14, 2001 (JP) .............................. 2001-278966

(51) Int. Cl.
G01N 27/416 (2006.01)

(52) U.S. Cl. .............................. 205/777.5; 204/403.01; 204/403.14

(58) Field of Classification Search ............ 204/403.01, 204/403.14; 205/777.5, 792

See application file for complete search history.

(56) References Cited

U.S. PATENT DOCUMENTS

| 4,545,382 A | 10/1985 | Higgins et al. |
| 5,205,920 A | 4/1993 | Oyama et al. |
| 5,582,697 A * | 12/1996 | Ikeda et al. ............... 205/777.5 |

(Continued)

FOREIGN PATENT DOCUMENTS

EP 1 176 202 A1 1/2002

(Continued)

OTHER PUBLICATIONS

Morris, N. A., Cardosi, M. F., Birch, B. J., Turner A. P. F., "An Electrochemical Capillary Fill Device for the Analysis of Glucose Incorporating Glucose Oxidase and Ruthenium (III) Hexamine as Mediator", Electroanalysis, vol. 4, 1992, pp. 1-9.*

(Continued)

*Primary Examiner*—Kaj K Olsen
(74) *Attorney, Agent, or Firm*—Hamre, Schumann, Mueller & Larson, P.C.

(57) ABSTRACT

The present invention relates to technology for constructing a reaction system including a test target, an oxidation-reduction enzyme, and an electron mediator, and measuring the concentration of the test target by an electrochemical process. A Ru compound is used as the electron mediator. The present invention provides a concentration test instrument including a substrate, first and second electrodes formed on the substrate, and a reagent layer formed as a solid. The reagent layer contains an oxidation-reduction enzyme and a Ru compound, and is constituted so as to dissolve and construct a liquid phase reaction system when a sample liquid is supplied.

2 Claims, 9 Drawing Sheets

U.S. PATENT DOCUMENTS 6,103,509 A * 8/2000 Sode .................. 435/190

FOREIGN PATENT DOCUMENTS

| JP | 03-287064 | * 12/1991 |
| --- | --- | --- |
| WO | WO 86/04926 | 8/1986 |
| WO | WO 01/57510 | 8/2001 |

OTHER PUBLICATIONS

Yum, D., Lee, Y., and Pan, J., "Cloning and Expression of a Gene Cluster Encoding Three Subunits of Membrane-Bound Gluconate Dehydrogenase from *Erwinia cypripedii* ATCC 29267 in *Escherichia coli*", Journal of Bacteriology, vol. 179, No. 21, 1997, pp. 6566-6572.*

Sode, K., Tsugawa, W., Yamazaki, T., Watanabe, M., Ogasawara, N., and Tanaka, M., "A novel thermostable glucose dehydrogenase varying temperature properties by altering its quaternary structures", Enzyme and Microbial Technology, vol. 19., 1996, pp. 82-85.*

Morris et al. "An electrochemical capillary fill device for the analysis of glucose incorporating glucose oxidase and ruthenium (III) hexamine as mediator". *Electroanalysis*, vol. 4, No. 1, pp. 1-9 (1992).

Okuda et al. "The application of cytochromes as the interface molecule to facilitate the electron transfer for PQQ glucose dehydrogenase employing mediator type glucose sensor". *Analytical Letters*, vol. 35, No. 9, pp. 1465-1478 (Jul. 2002).

Habermuller et al. "Electron transfer mechanisms in amperometric biosensors". *Fresenius Journal of Analytical Chemistry*, vol. 366, No. 6-7, pp. 560-568 (Mar. 2000).

* cited by examiner

CONCENTRATION MEASURING METHOD, CONCENTRATION TEST INSTRUMENT, AND CONCENTRATION MEASURING APPARATUS

This application is a 371 National Stage Entry of PCT/JP02/08855 filed on Aug. 30, 2002.

TECHNICAL FIELD

The present invention relates to technology for measuring a concentration of a test target (such as glucose or cholesterol) contained in a sample liquid (such as blood or another such biological sample, or a prepared liquid thereof).

BACKGROUND ART

Enzyme reactions are used as a way to quantify glucose concentration. In a typical case, glucose oxidase (GOD) is used as the enzyme. GOD is an enzyme which is linked to flavin adenine dinucleotide (FAD), which is a coenzyme. The enzyme reaction of glucose when GOD is used proceeds according to the following chemical formula (In the formula, $FADH_2$ is the reduction type of the FAD).

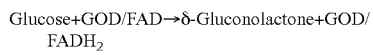
Glucose+GOD/FAD→δ-Gluconolactone+GOD/FADH$_2$

When blood sugar levels are measured in a clinical setting, glucose concentrations are sometimes quantified by measuring the change in absorbance, which corresponds to the change in glucose concentration. However, the most common method is to measure the glucose concentration by amperometry. Amperometry is widely employed as a method for measuring glucose concentration in portable blood sugar measurement devices.

An example of how blood sugar is measured by amperometry is given below, for the case of measuring oxidation current. In the first step, a reaction system is constructed using blood, an enzyme, and an oxidative electron transfer medium (mediator). The result is that the above-mentioned enzyme reaction proceeds while a reductive mediator is produced by an oxidation-reduction reaction between the mediator and the $FADH_2$ produced by this enzyme reaction. Potassium ferricyanide is commonly used as a mediator, in which case the reaction can be expressed by the following chemical formula.

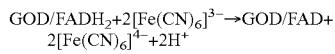
GOD/FADH$_2$+2[Fe(CN)$_6$]$^{3-}$→GOD/FAD+ 2[Fe(CN)$_6$]$^{4-}$+2H$^+$ Next, in the second step, voltage is applied to the reaction system using a pair of electrodes, which oxidizes the potassium ferrocyanide (releases electrons) and produces potassium ferricyanide as shown in the following chemical formula. The electrodes originating in the potassium ferrocyanide are supplied to the anode.

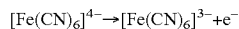
[Fe(CN)$_6$]$^{4-}$→[Fe(CN)$_6$]$^{3-}$+e$^-$

In the third step, the oxidation current value attributable to voltage application is measured, and the glucose concentration is computed on the basis of this measured value.

When blood sugar is measured using a portable blood sugar measurement device, a glucose sensor is used in which a reagent layer containing an enzyme and a mediator is formed between electrodes, and a reaction system is constituted between the electrodes by supplying blood to the reagent layer. This glucose sensor is installed in a portable blood sugar device, voltage is applied between the electrodes, the oxidation current value is measured, and the glucose concentration in the blood is quantified on the basis of this oxidation current value.

As discussed above, GOD is usually used as the enzyme, and potassium ferricyanide as the mediator. Nevertheless, in a reaction system combining GOD with potassium ferricyanide, the problems discussed below are encountered with a method for measuring glucose concentration by an electrochemical process, typified by amperometry.

The first of these problems is the effect of reductive substances. For instance, if we consider the measurement of glucose concentration in blood, there are reductive substances (such as ascorbic acid, glutathione, and Fe(II)$^{2+}$) coexisted in the blood in addition to glucose. If a reductive substance other than potassium cyanide is present when voltage is applied to the reaction system, electrons originating in the oxidation of the reductive substance caused by voltage application will be supplied to the electrodes in addition to the electrons originating in the potassium ferrocyanide. As a result, the measured current value will include background current (noise) attributable to the electron transfer of the reductive substance. Accordingly, the measured glucose concentration will end up being greater than the actual glucose concentration. The greater is the amount of voltage applied between the electrodes, the more types and quantity of reductive substances that are oxidized, and the more pronounced is this measurement error. Therefore, when potassium ferricyanide is used as the mediator, blood sugar cannot be measured accurately unless the final concentration is determined by correcting the measured value. This effect of reductive substances is not limited to when blood sugar is measured, and is similarly encountered with other components when the concentration is computed on the basis of the oxidation current value.

Another problem pertains to the storage stability of the glucose sensor when glucose concentration is measured with a portable blood sugar measurement device and a glucose sensor. Potassium ferricyanide is susceptible to the effects of light and water, and when exposed to these, receives electrons from sources other than glucose and turns into reductive potassium ferrocyanide. If this happens, then the reaction system will contain both potassium ferrocyanide that has been rendered reductive by enzyme reaction, and potassium ferrocyanide that has been rendered reductive by exposure. As a result, just as with the reductive substance problem described above, the oxidation current during voltage application includes background current originating in the potassium ferrocyanide resulting from exposure. Consequently, the measured glucose concentration ends up being greater than the actual glucose concentration. To minimize this problem, the glucose sensor must be sealed in a pouch made from a light-blocking material, for example, so that the reagent layer in the glucose sensor is not exposed. Furthermore, to extend the service life of the glucose sensor, it has to be sealed in a moisture-tight state by performing nitrogen replacement or other such treatment in order to avoid exposure to moisture, and this complicates manufacture and drives up the cost when the glucose sensor is mass-produced on an industrial scale.

DISCLOSURE OF THE INVENTION

It is an object of the present invention to provide technology that reduces the effect of background current at low cost, and allows the concentration of a test target in a sample liquid to be measured more accurately.

According to a first aspect of the present invention, there is provided a method for measuring the concentration of a test target, whereby a reaction system is constituted to include the test target, an oxidation-reduction enzyme and an electron mediator, and then the concentration of the test target is measured by utilizing an electrochemical process. For the electron mediator, use is made of a Ru compound.

The above concentration measuring method may preferably comprise a first step of producing a reductant of the Ru compound in the reaction system, a second step of applying voltage to the reaction system to oxidize the reductant, and measuring the response current value correlated with the quantity of electrons released by the reductant at this time, and a third step of calculating the concentration of the test target on the basis of the response current value measured in the second step.

With the method of the present invention, the first step may be conducted with the reaction system in a voltage non-application state and the second step then conducted with the reaction system in a voltage application state, or the first and second steps may be conducted simultaneously with the reaction system in a voltage application state continuously from the time the sample liquid containing at least the test target is supplied.

The voltage applied between the first and second electrodes in the second step is preferably a constant potential, and the value thereof is preferably at least a standard oxidation-reduction potential (versus a standard hydrogen electrode) between the reductive Ru(II) complex and the oxidative Ru(III) complex, and less than a standard oxidation-reduction potential (versus a standard hydrogen electrode) between ferrocyanide ions and ferricyanide ions. The constant voltage applied between the first and second electrodes may be 100 to 500 mV, for example, and more preferably 100 to 300 mV.

Preferably, the first step lasts from 0 to 10 seconds, and the current value measured after a specific amount of time has elapsed (at least 3 seconds) from the start of the second step is employed as a computational current value that serves as the basis for computation of the glucose concentration in the third step. Even more preferably, the first step lasts from 0 to 3 seconds, and the current value measured after a specific amount of time has elapsed (3 to 5 seconds) from the start of the second step is employed as the computational current value.

According to a second aspect of the present invention, there is provided a concentration test instrument comprising a substrate, first and second electrodes formed on the substrate, and a reagent layer formed as a solid. The reagent layer may comprise an oxidation-reduction enzyme and a Ru compound, and may be constituted so as to dissolve and construct a liquid phase reaction system when a sample liquid containing the test target is supplied.

Preferably, the reagent layer is constituted such that when the sample liquid is supplied, an oxidation-reduction enzyme and a Ru compound are both present in the liquid phase reaction system.

Preferably, in the first and second aspects of the present invention, the Ru compound is present in the reaction system as an oxidative Ru complex. There are no particular restrictions on the type of ligand in the Ru complex as long as the complex functions as a mediator (electron transfer medium), but it is preferable to use an oxidative type expressed by the following chemical formula.

Examples of X in the chemical formula include $NH_3$, a halogen ion, CN, pyridine, nicotinamide, and $H_2O$, but $NH_3$ or a halogen ion is preferable. $n^+$ in the chemical formula is the valence of the oxidative Ru(III) complex as determined by the type of X.

If the Ru compound is an oxidative Ru(III) complex, then the electron transfer system is selected so that the reductive Ru(II) complex will be produced by only two reactions: an oxidation reaction of the measurement test target catalyzed by the oxidation-reduction enzyme, and a reduction reaction of the oxidative Ru(III) complex.

The reaction system is constituted, for example, as a uniform or substantially uniform liquid phase reaction system in which a relatively small amount of the oxidation-reduction enzyme is dispersed uniformly or substantially uniformly with respect to a relatively large amount of the oxidative Ru(III) complex. In this case, the reductant is produced substantially uniformly in every location of the reaction system.

Examples of the test target include glucose, cholesterol, lactic acid, and ascorbic acid.

The oxidation-reduction enzyme is selected according to the type of test target, but preferably is at least one type selected from the group consisting of glucose dehydrogenase (GDH) (including the αGDH and CyGDH discussed below), glucose oxidase (GOD), cholesterol dehydrogenase, cholesterol oxidase, lactic acid dehydrogenase, lactic acid oxidase, ascorbic acid dehydrogenase, ascorbic acid oxidase, alcohol dehydrogenase, alcohol oxidase, fructose dehydrogenase, 3-hydroxybutyric acid dehydrogenase, pyruvic acid oxidase, NADH oxidase, uric acid oxidase (uricase), urease, and dihydrolipoamide dehydrogenase (diaphorase).

With the present invention, examples of GDH that can be used include types in which pyrroquinoline quinone (PQQ), nicotinamide adenine dinucleotide (NAD), nicotinamide adenine dinucleotide phosphate (NADP), or another such compound serves as a coenzyme, as well as αGDH, CyGDH, and so forth. It is preferable for the GDH to be αGDH, CyGDH, or a compound in which PQQ serves as a coenzyme (PQQGDH).

αGDH contains a GDH-active protein whose molecular weight is approximately 60 kDa in SDS-polyacrylamide gel electrophoresis under reduction conditions as subunits having glucose dehydrogenation activity. CyGDH, meanwhile, contains as subunits the above-mentioned GDH-active protein and an electron mediator protein (cytochrome C) whose molecular weight in SDS-polyacrylamide gel electrophoresis under reduction conditions is approximately 43 kDa. The GDH can also be one further having subunits other than a GDH-active protein and cytochrome C.

CyGDH can be obtained by refining an enzyme externally secreted by a microbe belonging to *Burkholderia cepacia*, or by refining an enzyme found internally in this microbe. αGDH, meanwhile, can be obtained by forming a transformant implanted with a gene coding for the expression of αGDH collected from a microbe belonging to *Burkholderia cepacia*, for example, and refining an enzyme externally secreted from this transformant, or refining an enzyme found internally in this transformant.

As for the microbe belonging to *Burkholderia cepacia*, for example, *Burkholderia cepacia* KS1 strain can be used. This KS1 strain deposited on Sep. 25, 2000 as microorganism deposit number FERM BP-7306 with the Patent Organism Depositary of the National Institute of Advanced Industrial Science and Technology (Chuo No. 6, 1-1, Higashi 1-chome, Tsukuba-shi, Ibaraki, Japan, 305-8566).

According to a third aspect of the present invention, there is provided a concentration measuring apparatus which is used together with a concentration test instrument including a reagent layer a first electrode and a second electrode, where the reagent layer contains a Ru compound as an oxidation-reduction enzyme. The measuring apparatus includes a voltage applier for applying voltage between the first and second electrodes, a current value measurer for measuring the response current value when voltage has been applied between the first and second electrodes, and a computer for computing the concentration of the test target on the basis of the response current value.

Preferably, the concentration measuring apparatus may further comprise a controller for controlling the voltage application performed by the voltage applier, or for controlling the current value measurement performed by the current value measurer.

The above controller is constituted, for example, such that the voltage applied by the voltage applier is controlled to be a constant voltage selected from a range of 100 to 500 mV, and preferably 100 to 300 mV. The controller may also be constituted such that the voltage applied by the voltage applier is controlled to be a constant voltage selected from a range of at least a standard oxidation-reduction potential (versus a standard hydrogen electrode) between the oxidant and reductant of the Ru compound, and less than a standard oxidation-reduction potential (versus a standard hydrogen electrode) between ferrocyanide ions and ferricyanide ions.

Preferably, the concentration measuring apparatus of the present invention may further comprise a detector for detecting that a sample liquid has been supplied to the reagent layer of the concentration test instrument. The controller is constituted, for example, so as to control the voltage applier such that no voltage is applied between the first and second electrodes during a first specific period of 0 to 10 seconds after the detector has detected that a sample liquid has been supplied to the reagent layer. In this case, the control means controls the voltage applier such that a specific potential is applied between the first and second electrodes by the voltage applier starting at the point when the first time period has elapsed. The control means is further constituted such that the response current value used for concentration computation by the computer is measured by the current value measurer at a point when a second specific time period of at least 3 seconds has elapsed after the start of the previous application of the specific potential. Preferably, the first specific time period is 0 to 3 seconds, and the second specific time period is 3 to 5 seconds.

BEST MODE FOR CARRYING OUT THE INVENTION

Preferred embodiments of the present invention will now be described with reference to the drawings. In these embodiments, the description will be for examples of a glucose concentration measuring apparatus and glucose sensor constituted such that the glucose concentration in a sample liquid is measured. However, the present invention is not limited to the measurement of glucose concentration, and can also be applied to the measurement of other components.

Figure 1:
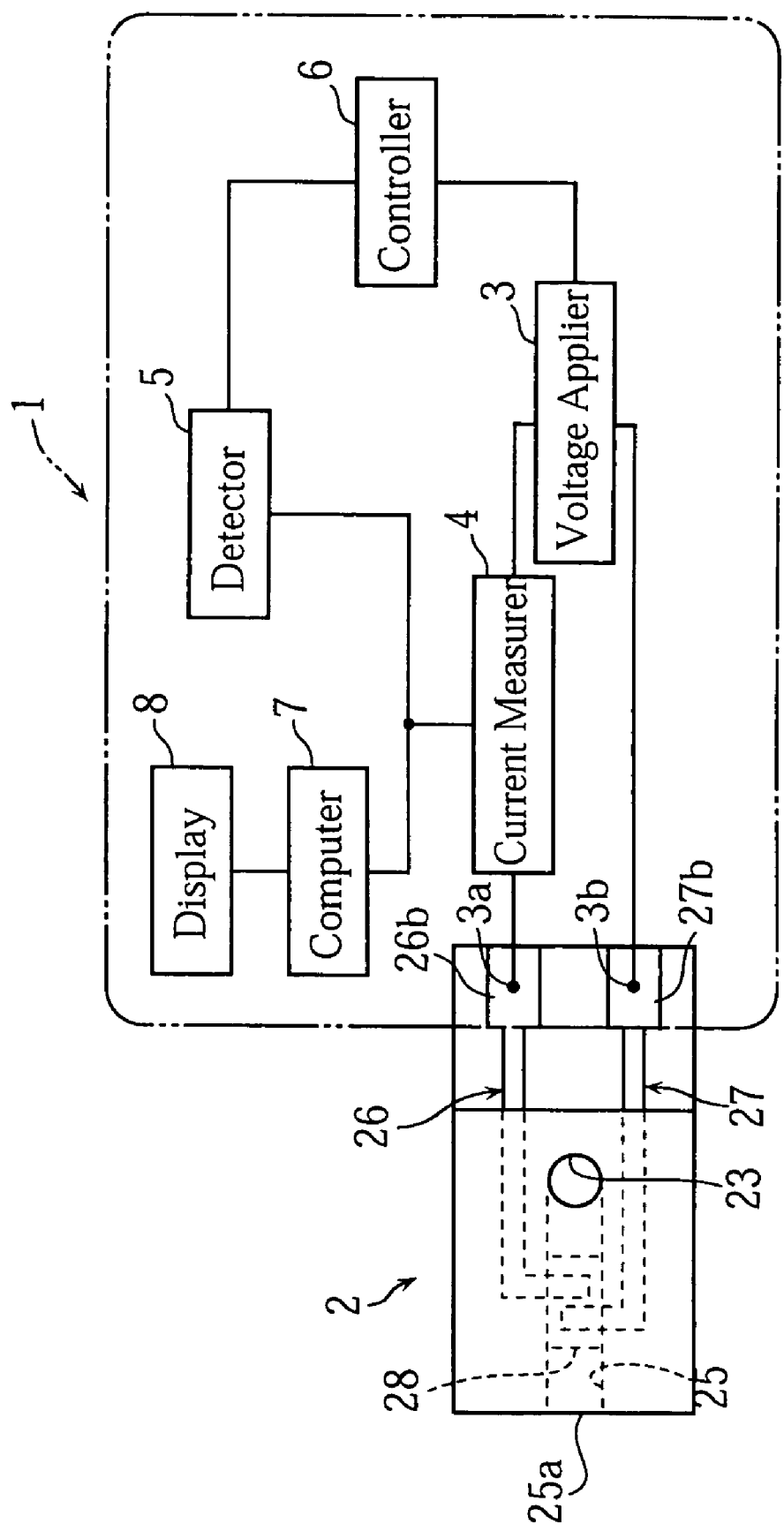
FIG. 1 is a schematic diagram illustrating the basic structure in a glucose concentration measuring apparatus according to the present invention.

As shown in FIG. 1, a glucose concentration measuring apparatus 1 uses a glucose sensor 2 to measure the glucose concentration in a glucose solution such as blood. This glucose concentration measuring apparatus 1 comprises a voltage applier 3, a current measurer 4, a detector 5, a controller 6, a computer 7, and a display unit 8.

Figure 2:
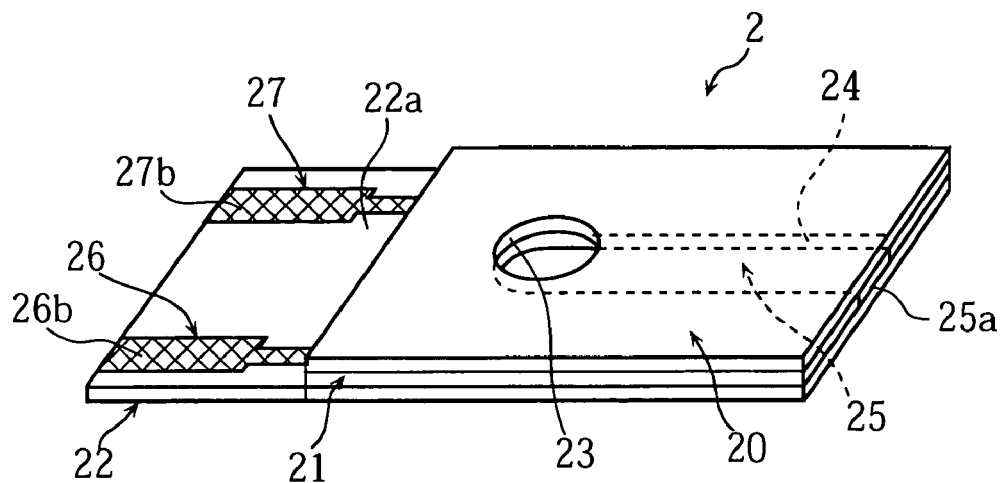
FIG. 2 is an overall oblique perspective view illustrating a glucose sensor used in the glucose concentration measuring apparatus in FIG. 1.
Figure 3:
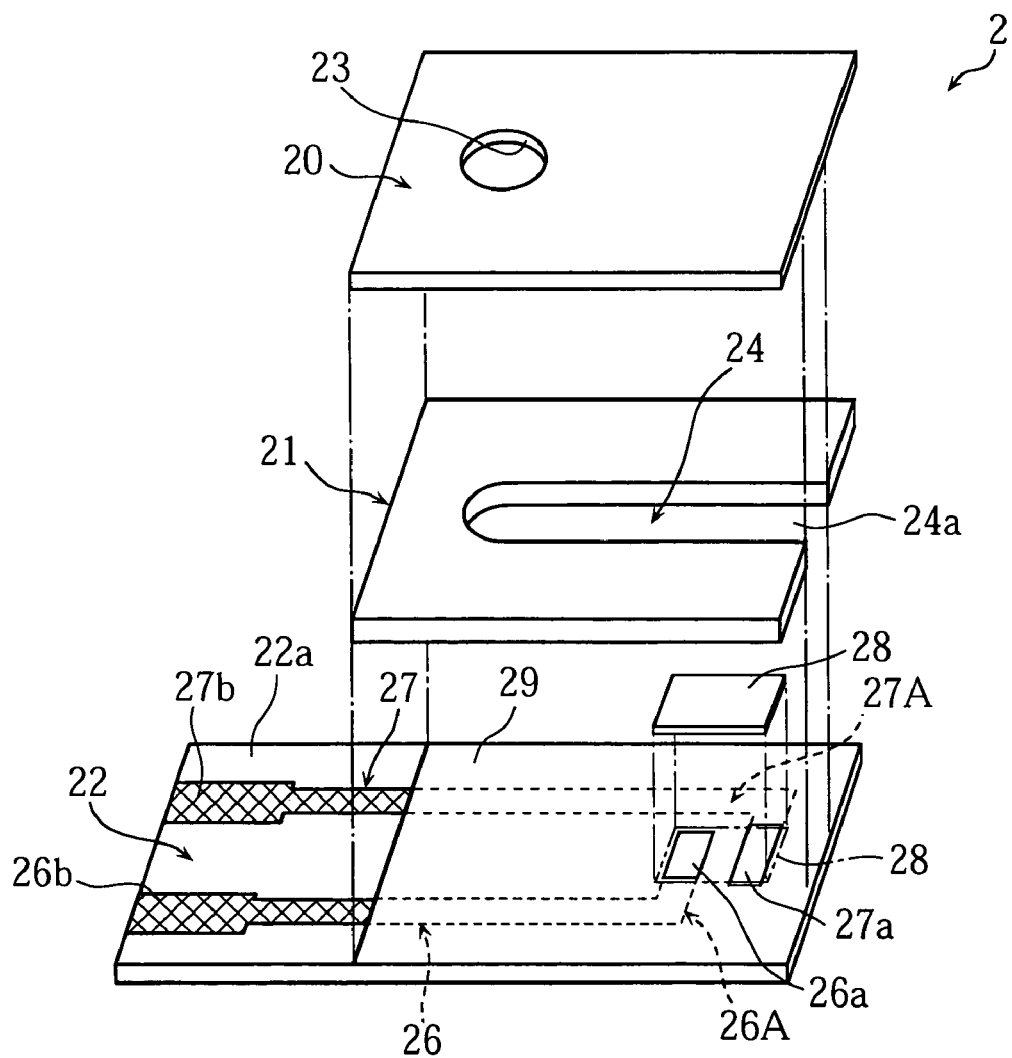
FIG. 3 is an exploded oblique perspective view of the glucose sensor in FIG. 2.

As clearly shown in FIGS. 2 and 3, the glucose sensor 2 includes a cover plate 20, a spacer 21, and a base plate 22. A channel 25 is created by these members.

A hole 23 is made in the cover plate 20, and a slit 24 that communicates with the hole 23 and is open at its distal end 24a is provided to the spacer 21. The channel 25 communicates with the outside via the hole 23 and the open distal end 24a of the slit 24. The distal end 24a constitutes a sample liquid introduction opening 25a. Glucose solution supplied through this sample liquid introduction opening 25a moves by capillary action through the channel 25 toward the hole 23.

A first electrode 26, a second electrode 27, and a reagent layer 28 are provided on the upper surface 22a of the base plate 22.

The first and second electrodes 26 and 27 generally extend in the longitudinal direction of the base 22. The first and second electrodes 26 and 27 have at their ends 26A and 27A a working portion 26a and a counterpart portion 27a extending in parallel to the shorter sides of the base plate 22.

The upper surface 22a of the base plate 22 is covered by an insulating film 29 so as to expose the working portion 26a of the first electrode 26, the counterpart portion 27a of the second electrode 27, and the opposite ends 26b and 27b of the first and second electrodes 26 and 27. As discussed below, the opposite ends 26b and 27b of the first and second electrodes 26 and 27 constitute terminals for providing contact with first and second contacts 3a and 3b (see FIG. 1) of the glucose concentration measuring apparatus 1.

The reagent layer 28 is, for example, in solid form and provided so as to span the distance between the working portion 26a and the counterpart portion 27a. This reagent layer 28 includes, for example, a relatively large amount of mediator (electron transfer medium) and a relatively small amount of the oxidation-reduction enzyme. The reagent layer 28 is formed, for example, by applying a coating of paint, in which the mediator and the oxidation-reduction enzyme are substantially uniformly dispersed, so as to span the distance between the first and second electrodes 26 and 27, and then drying this coating. When the reagent layer 28 is formed in this way, it becomes a single, solid layer in which the oxidation-reduction enzyme is substantially uniformly dispersed in the mediator, and is readily dissolved by the supply of the glucose solution.

It is preferable to use glucose dehydrogenase (GDH) or glucose oxidase (GOD) as the oxidation-reduction enzyme. The GDH can be a type in which such compounds as pyrroquinoline quinone (PQQ), nicotinamide adenine dinucleotide (NAD) or nicotinamide adenine dinucleotide phosphate (NADP) serve as a coenzyme, or can be αGDH or CyGDH. Of these GDHs, it is preferable to use αGDH, CyGDH, or a compound in which PQQ serves as a coenzyme (i.e., PQQGDH).

A Ru complex, for example, is used as the mediator. There are no particular restrictions on the type of ligand in the Ru complex as long as the complex functions as an electron transfer medium, but it is preferable to use an oxidative type expressed by the following chemical formula.

$$[Ru(NH_3)_5X]^{n+}$$

Examples of X in the chemical formula include $NH_3$, a halogen ion, CN, pyridine, nicotinamide, and $H_2O$, but $NH_3$ or a halogen ion is preferable. $n^+$ in the chemical formula is the valence of the oxidative Ru(III) complex, which is determined by the type of X.

Ru complexes are usually in the form of an oxidative type (III) because reductive types (II) are unstable. Accordingly, the Ru complex will not readily undergo undesirable reduction even when exposed to light or water when mixed into the reagent layer 28 of the glucose sensor 2. Another characteristic of a Ru complex is that it does not readily crystallize and can be suitably maintained in the form of a micropowder. Another advantage, at least for combinations of Ru complex and PQQGDH, is fast electron transfer.

The voltage applier 3 shown in FIG. 1 applies a constant voltage between the terminal 26b of the first electrode 26 and the terminal 27b of the second electrode 27. The voltage applier 3 is designed so that when the glucose sensor 2 is mounted in its mounting component (not shown) provided to the glucose concentration measuring apparatus 1, there is electrical continuity between the terminals 26b and 27b of the glucose sensor 2 via the first and second contacts 3a and 3b. A DC power supply such as a dry cell or a rechargeable cell is used as the voltage applier 3.

The current measurer 4 measures the response current value correlated with the quantity of electrons released from the reductive Ru(II) complex of the reagent layer 28 when voltage is applied between the first and second electrodes 26 and 27.

After the glucose sensor 2 is mounted in the glucose concentration measuring apparatus 1, the detector 5 detects whether or not a glucose solution has been supplied to the reagent layer 28 and measurement of the glucose concentration is possible.

The controller 6 controls the voltage applier 3 and selects between states in which voltage is applied (closed circuit) and is not applied (open circuit) between the first and second electrodes 26 and 27. The controller 6 also controls the current value measurement timing in the current measurer 4.

The computer 7 computes the glucose concentration in the glucose solution according to the response current value measured by the current measurer 4.

The detector 5, the controller 6, and the computer 7 are each constituted by a CPU and a memory such as a ROM or RAM, for example, but it is also possible to constitute all of the detector 5, the controller 6, and the computer 7 by connecting a plurality of memories to a single CPU. The computation results of the computer 7 are displayed by the display unit 8. The display unit 8 is constituted by an LCD or the like.

Next, the procedure for measuring the glucose concentration in a glucose solution will be described through reference to FIGS. 4 and 5 in addition to FIGS. 1 to 3.

As is clearly shown in FIG. 1, first the glucose sensor 2 is installed in the glucose concentration measuring apparatus 1. As a result, the terminals 26b and 27b of the first and second electrodes 26 and 27 of the glucose sensor 2 come into contact with the first and second contacts 3a and 3b of the glucose measuring apparatus 1. As was mentioned above, there is electrical continuity between the first and second electrodes 26 and 27 and the voltage applier 3 in this state. In actual measurement, a constant voltage is applied between the first and second electrodes 26 and 27 by the voltage applier 3 under the control of the controller 6 even before the glucose solution is supplied to the glucose sensor 2.

The constant voltage applied between the first and second electrodes 26 and 27 is set to within a range of 100 to 500 mV, for instance. Preferably, the constant voltage is at least a standard oxidation-reduction potential (versus a standard hydrogen electrode) between the reductive Ru(II) complex and the oxidative Ru(III) complex, and less than a standard oxidation-reduction potential (versus a standard hydrogen electrode) between ferrocyanide ions and ferricyanide ions. The standard oxidation-reduction potential of a Ru complex varies somewhat with the type of ligands, but is roughly +100 mV, while that of ferricyanide ions is +360 mV. Therefore, the constant voltage applied between the first and second electrodes 26 and 27 by the voltage applier 3 is selected from a range of 100 to 350 mV, for example. It was discussed above that it is best for the Ru complex to be an oxidative type expressed by $[Ru(NH_3)_8]^{3+}$ (or a reductive type expressed by $[Ru(NH_3)_6]^{2+}$). Here again, the constant voltage is preferably 100 to 350 mV, and even more preferably 100 to 300 mV.

Next, a glucose solution such as blood is supplied through the sample liquid introduction opening 25a of the glucose sensor 2. The glucose solution moves by capillary action through the channel 25 of the glucose sensor 2. In the course of this movement the glucose solution dissolves the reagent layer 28.

As touched upon above, since a Ru complex does not readily crystallize and can be suitably maintained in the form of a micropowder, if a Ru complex is contained in the form of a micropowder in the reagent layer 28, the entire reagent layer 28 will readily and instantly dissolve when the glucose solution is supplied. Because the reagent layer 28 comprises a Ru complex dispersed in an oxidation-reduction enzyme, an enzyme reaction occurs uniformly at every location of the reagent layer 28, which allows the glucose concentration to be measured accurately in a short time.

Meanwhile, if a glucose solution is supplied to the reagent layer 28, the glucose is oxidized into gluconolactone and the mediator is made into a reductive type by the oxidation-reduction enzyme. Since the mediator is substantially uniformly dispersed in the reagent layer 28, a reductive mediator is produced spontaneously, without any voltage being applied, substantially uniformly at every location of the reagent layer 28. The gluconolactone becomes gluconic acid without the help of the enzyme.

Figure 4A:
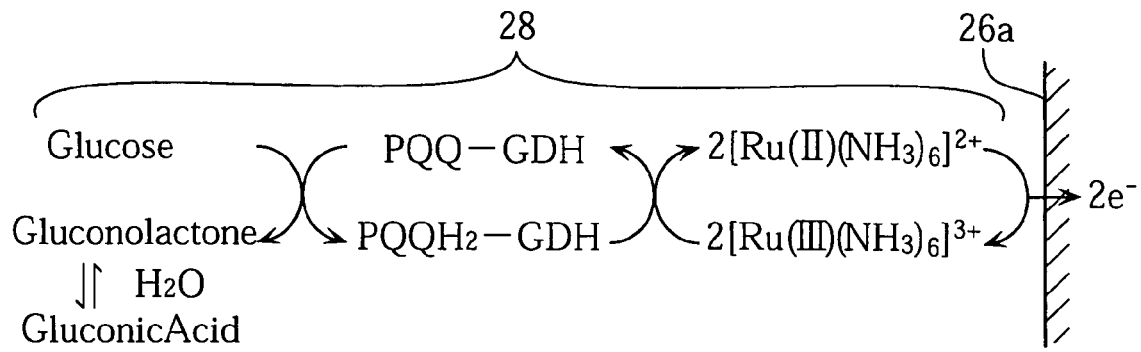
FIG. 4A is a diagram of the electron transfer system in a reaction system including PQQ-GDH and a Ru complex.
Figure 4B:
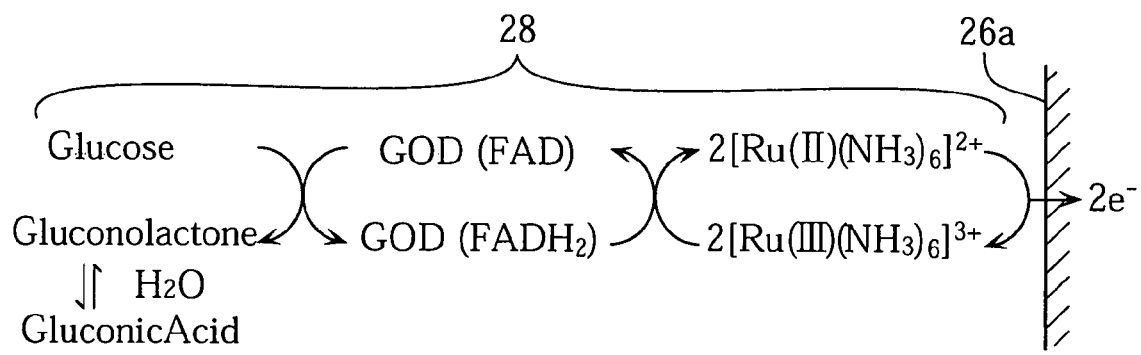
FIG. 4B is a diagram of the electron transfer system in a reaction system including GOD and a Ru complex.

Here, FIG. 4A is a diagram of the electron transfer system when $[Ru(III)(NH_3)_6]^{3+}$ is used as the mediator and PQQGDH is used as the oxidation-reduction enzyme, while FIG. 4B is a diagram of the electron transfer system when $[Ru(III)(NH_3)_6]^{3+}$ is used as the mediator and GOD is used as the oxidation-reduction enzyme.

In the example depicted in FIGS. 4A and 4B, in a state in which constant voltage is applied between the first and second electrodes 26 and 27 via the two terminals 26b and 27b, the reductive Ru(II) complex present in the reagent layer 28 moves to the working portion 26a side of the first electrode 26, releases electrons to this working portion 26a, and creates an oxidative Ru(II) complex. Therefore, in a state in which constant voltage is applied between the first and second electrodes 26 and 27 by the voltage applier 3, the quantity of electrons given off by the reductive Ru(II) complex is measured as the response current value by the current measurer 4 via the first electrode 26 and the first contact 3a. This response current value is correlated with the quantity of electrons originating in the reductive Ru(II) complex that has moved through the reagent layer 28 as a result of voltage application, and is known as the diffusion current.

Figure 5:
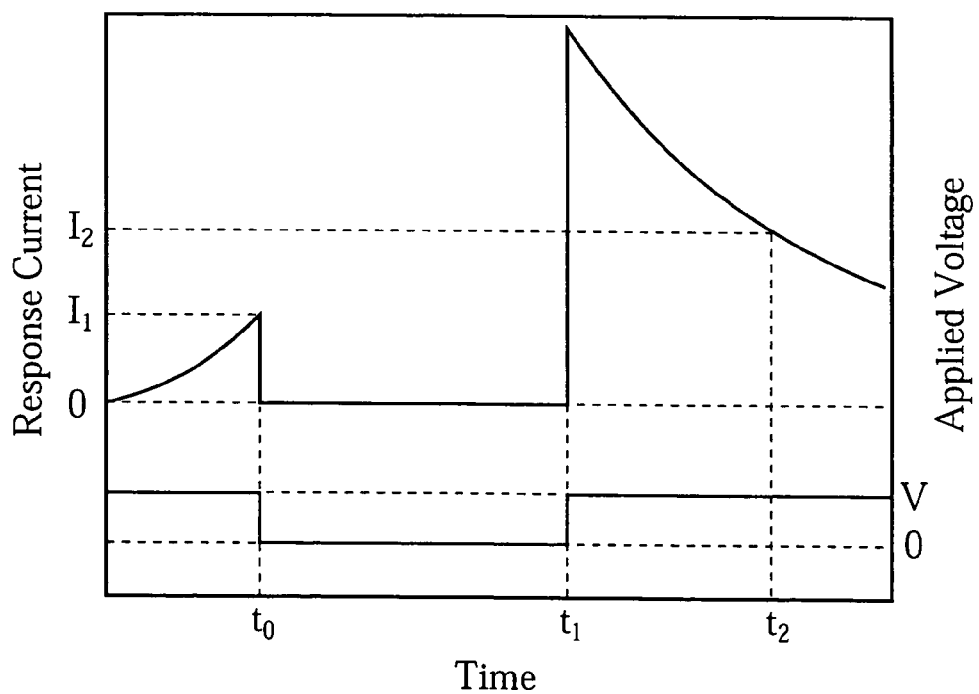
FIG. 5 is a graph of the change over time in the voltage applied to the first and second electrodes and the response current value in measurement of the glucose concentration.

Meanwhile, the response current value measured by the current measurer 4 is monitored by the detector 5, and as shown in FIG. 5, the detector 5 detects that the glucose solution has been supplied to the reagent layer 28 and the reagent layer 28 has dissolved at the point $t_0$ when the response current value exceeds a threshold $I_1$ (such as 2 to 3 µA).

When the detector 5 has detected that the glucose solution has been supplied, the controller 6 controls the voltage applier 3 and halts the application of voltage between the first and second electrodes 26 and 27. Since the reductive Ru(II) complex is not oxidized while voltage application is halted, the reductive Ru(II) complex accumulates as a result of the glucose oxidation reaction and the mediator reduction reaction brought about by the oxidation-reduction enzyme. At a point $t_1$ when a specific amount of time has elapsed (such as $t_1$-$t_0$=0 to 10 seconds, and preferably 0 to 3 seconds), a constant voltage V is applied between the first and second electrodes 26 and 27 by the voltage applier 3 under the control of the controller 6. Even after the detector 5 has detected that the glucose solution has been supplied, application of voltage may be continued so that the produced reductive Ru(II) complex is successively moved to the working portion 26a and the diffusion current is measured.

Here, as shown in FIGS. 4A and 4B, a reductive Ru(II) complex releases electrons e⁻ to become an oxidative Ru(III) complex. When other reductive substances are present in the glucose solution along with a reductive Ru(II) complex, these substances also release electrons in according to the type and amount of component corresponding to the applied voltage, and become oxidative.

The electrons released by the reductive Ru(II) complex and any other reductive substances are supplied to the working portion 26a of the first electrode 26 and are measured as the response current value by the current measurer 4 via the first contact 3a. Therefore, the response current value that is actually measured includes that produced by electrons originating in the coexistent substances that became oxidative upon the application of voltage. The probability (proportion) at which the coexistent substances that were reductive release electrons and become oxidative is dependent on the amount of voltage applied to the first and second electrodes 26 and 27; the more voltage applied, the more types of the coexistent substances release electrons and the greater the total amount of electrons released by the individual substances. Also, the reductive R(II) complex can include not only one that has been given electrons in the oxidation-reduction reaction with the oxidation-reduction enzyme, but also one that has been made into reductive Ru(II) through exposure to water or light. Accordingly, the response current value that is actually measured can include background current attributable to the reductive Ru(II) originating in electrodes from something other than an enzyme reaction, or background noise due to the coexistent substance that are present.

In contrast, according to the present embodiment, as is clear from FIG. 5, the constant voltage V applied to the first and second electrodes 26 and 27 is the same as the constant voltage V applied up to the point when the detector detects that the glucose solution has been supplied to the reagent layer 28. Specifically, the reapplied constant voltage V is between 100 and 350 mV, and preferably 100 to 300 mV, which is less than the standard oxidation-reduction potential of a ferricyanide ion. With this, the voltage applied to the first and second electrodes 26 and 27 is less than when a ferricyanide ion (potassium) is used as the mediator. This makes it possible to suppress the oxidation (release of electrons) of the reductive coexistent substances such as ascorbic acid or glutathione that are also present when blood or the like is used as the glucose solution, which would otherwise occur upon the application of voltage. This reduces the background current caused by the effect of the reductive coexistent substances present in the solution. As a result, it is possible to compute the concentration with good precision even without factoring in the effect of these reductive coexistent substances and correcting the measured values.

Also, because an oxidative Ru(III) complex is far more stable than a reductive Ru(II) complex, this Ru complex is less apt to decompose in the presence of moisture or under optical irradiation, and most of it remains as oxidative Ru(III) until given electrons by an enzyme reaction. Therefore, the proportion of Ru(III) complex that has been rendered reductive by electrons from sources other than an enzyme reaction is far smaller, and this again allows background current to be reduced. Accordingly, there is no need to give much thought to the effect of moisture in the storage of the glucose sensor 2, so there is no need to reduce the amount of moisture by means of nitrogen replacement or the like. As a result, manufacturing is correspondingly easier when the glucose sensor 2 is mass-produced on an industrial scale, and this keeps the cost lower.

Furthermore, in the present embodiment, diffusion current based on the reductive Ru(II) complex produced by the entire reagent layer 28 is measured as the response current. In other words, since the two oxidation-reduction reactions shown in FIGS. 4A and 4B occur at every location of the reagent layer 28, the glucose reaction is concluded as soon as the glucose solution is supplied. Accordingly, if the glucose concentration is about 600 mg/dL, the oxidative Ru(III) complex will be converted into reductive Ru(II) in an amount corresponding to the glucose concentration at the point when the response current value is measured, such as 5 seconds after the glucose is supplied. Therefore, the response current value will be relatively large (on the µA level) even through the glucose concentration is on the 100 mg/dL level, and is therefore less affected by noise from electromagnetic waves and so forth. This means that the glucose concentration can be measured with good precision without having to take such steps as ensuring a large electrode surface area. Also, high concentration levels are difficult to measure when, for example, a mediator or enzyme is fixed to electrodes, the enzyme is subjected to a catalytic reaction on just the surface of the electrodes, electrons are exchanged between the mediator and the electrodes, and the amount of electron movement here (catalyst current) is measured. In other words, if even one of the plurality of reactions participating in the exchange of electrons between glucose and the electrodes is slower than the other reactions, that reaction will become the rate-limiting stage, and even if glucose is supplied over a specific concentration, the response current value will not rise over a specific value. Consequently, the response current value gradually approaches a constant value within a range in which the glucose concentration is relative high, making it difficult to measure high concentrations. In contrast, when diffusion current value is measured, the response current value is measured at the point when the glucose reaction has actually concluded, so glucose concentrations can be appropriately measured even at relatively high concentration levels.

Meanwhile, the computer 7 computes the glucose concentration in a glucose solution on the basis of the response current $I_2$ measured by the current measurer 4 at the point $t_2$ when a specific time (such as $t_2-t_1$=at least 3 seconds, and preferably 3 to 5 seconds) has elapsed since the reapplication of voltage between the first and second electrodes 26 and 27. The glucose concentration is computed by converting the response current value into a voltage value, then checking this voltage value against a calibration curve which is produced ahead of time and expresses the relationship between voltage and glucose concentration. This calibration curve is, for example, converted into data and stored in a ROM along with the program for executing computation. The glucose concentration is computed by utilizing a CPU or RAM to execute the program stored in this ROM.

EXAMPLES

It will be proven below by Examples 1 to 8 that when a Ru complex is used as a mediator in the measurement of glucose concentration by utilizing an enzyme reaction, the glucose concentration can be measured in a short time and at a low voltage, any reductive substances contained in the glucose solution have little effect, resistance to exposure to light or water is high, and the solubility of the reagent layer is high.

(Production of Glucose Sensor)

A glucose sensor with a first electrode, a second electrode, a reagent layer and a channel formed on a substrate as shown in FIGS. 2 and 3, was used in Examples 1 to 8. The first and second electrodes were formed on the substrate by screen printing with a carbon paste.

Two glucose sensors were compared in Examples 1 to 6. One of these is termed glucose sensor 1 and the other comparative glucose sensor 1. The difference between these glucose sensors was in the formulation of their reagent layers, as shown in Table 1 below. These reagent layers were formed by applying spots of 1 µL of reagent composed of an oxidation-reduction enzyme and a potassium phosphate buffer on a substrate, and then drying.

TABLE 1

| | Formulation of Reagent Layer | | |
|---|---|---|---|
| | Mediator | Oxidation-reduction enzyme | Buffer (pH 7) |
| Glucose sensor 1 of present invention | 300 mM [Ru (III) (NH$_3$)$_6$]Cl$_3$ | 5000 U/mL PQQGDH | 50 mM potassium phosphate |
| Comparative glucose sensor 1 | 300 mM K$_3$[Fe (III) (CN)$_6$] | 5000 U/mL PQQGDH | 50 mM potassium phosphate |

In Example 7, two glucose sensors 2 and 3 of the present invention comprising a different oxidation-reduction enzyme from that used in Examples 1 to 6 were used as indicated in Table 2 below. Other than the constitution of the reagent layer, these were the same as the glucose sensors in Examples 1 to 6. αGDH and CyGDH were as discussed previously.

TABLE 2

| | Formulation of Reagent Layer | | |
|---|---|---|---|
| | Mediator | Oxidation-reduction enzyme | Buffer (pH 7) |
| Glucose sensor 2 of present invention | 300 mM [Ru (III) (NH$_3$)$_6$]Cl$_3$ | 600 U/mL CyGHD | 250 mM potassium phosphate |
| Glucose sensor 3 of present invention | 300 mM [Ru (III) (NH$_3$)$_6$]Cl$_3$ | 600 U/mL αGDH | 250 mM potassium phosphate |

A glucose sensor 4 of the present invention and a comparative glucose sensor 2 in which GOD was used as the oxidation-reduction enzyme as shown in Table 3 below were used in Example 8. Other than the constitution of the reagent layer, these were the same as the glucose sensors in Examples 1 to 6.

TABLE 3

| | Formulation of Reagent Layer | | |
|---|---|---|---|
| | Mediator | Oxidation-reduction enzyme | Buffer (pH 7) |
| Glucose sensor 4 of present invention | 300 mM [Ru (III) (NH$_3$)$_6$]Cl$_3$ | 5000 U/mL GOD | 50 mM potassium phosphate |
| Comparative glucose sensor 2 | 300 mM K$_3$[Fe (III) (CN)$_6$] | 5000 U/mL GOD | 50 mM potassium phosphate |

Example 1

Figure 6:
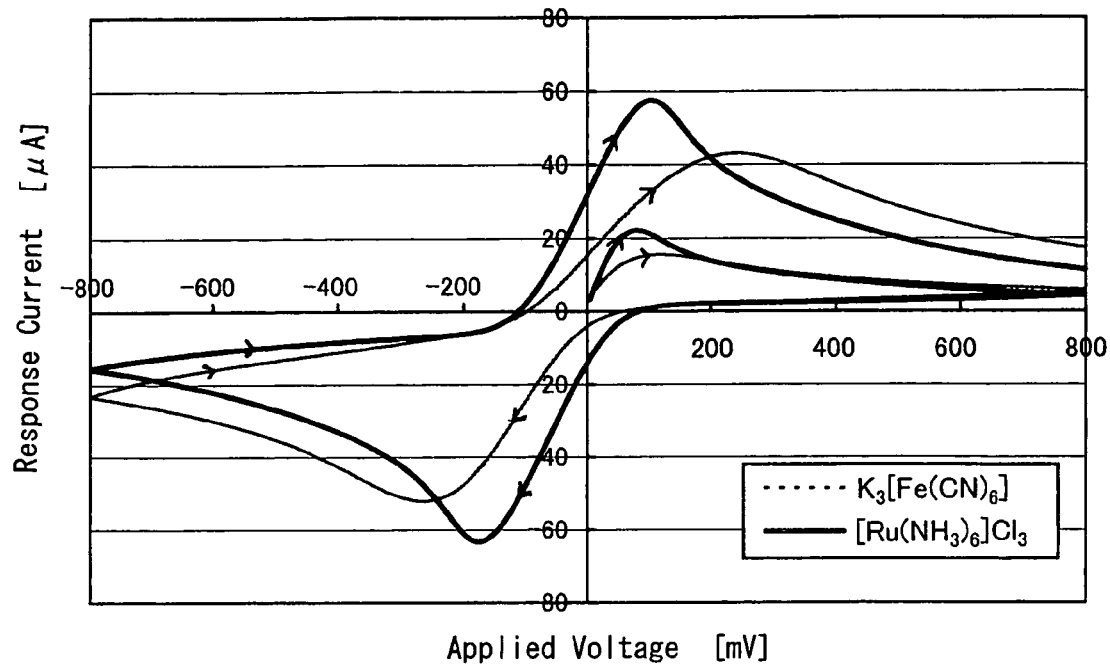
FIG. 6 is a graph of the CV waveforms of a glucose sensor 1 of the present invention and a comparative glucose sensor.

In this example, the electrode response characteristics of glucose sensors were evaluated by examining CV waveforms. The CV waveform was examined by applying spots of glucose solution on the reagent layer of the glucose sensor, sweeping such that the sweep rate was 50 mV/sec and the applied voltage was 0 mV→+800 mV→0 mV→−800 mV→0 mV→+800 mV, and measuring the response current during the sweep. The glucose solution used here was a standard solution with a concentration of 200 mg/dL (prepared by dissolving glucose in physiological saline (0.9 wt % NaCl)). The amount of spot application of the glucose solution on the reagent layer was 1 μL. FIG. 6 shows the CV waveforms.

It can be seen from the CV waveforms in FIG. 6 that within a range in which the applied voltage was 0 mV→+800 mV on the second time, the response current value was at its maximum when the applied voltage was approximately 100 mV with the glucose sensor 1 of the present invention in which [Ru(III)(NH$_3$)$_6$]Cl$_3$ was used as the mediator, whereas the response current value reached its maximum at slightly less than 300 mV with the comparative glucose sensor 1 in which K$_3$[Fe(III)(CN)$_6$] was used. The CV waveforms in FIG. 6 tell us that when [Ru(III)(NH$_3$)$_6$]Cl$_3$ is used as the mediator, if the applied voltage is set at 100 mV or higher, substantially all of the reductive compounds can be oxidized and made oxidative, and similarly that when K$_3$[Fe(III)(CN)$_6$] is used, the applied voltage must be at least 300 mV. The applied voltage at which the response current value of each mediator reached its maximum substantially matched the standard oxidation-reduction potential for each mediator.

Therefore it can be concluded that if a Ru complex with a low standard oxidation-reduction potential is used as the mediator, glucose concentration can be measured favorably even at a low applied voltage, and that in this case measurement at good precision is made possible by decreasing the background current caused by other reductive substances present in the solution.

Example 2

In this example, it was examined whether glucose concentration can be accurately measured at a low voltage (200 mV). To this end, the response current value was measured using four different standard solutions with glucose concentrations of 0 mg/dL, 200 mg/dL, 400 mg/dL, and 600 mg/dL and using the glucose sensor 1 of the present invention and the comparative glucose sensor 1, at applied voltages of 500 mV and 200 mV. The response current value was measured 5 seconds after the spot application of 1 μL of standard solution to the reagent layer, with the application of voltage held steady between the first and second electrodes. These results are given in FIG. 7.

Figure 7:
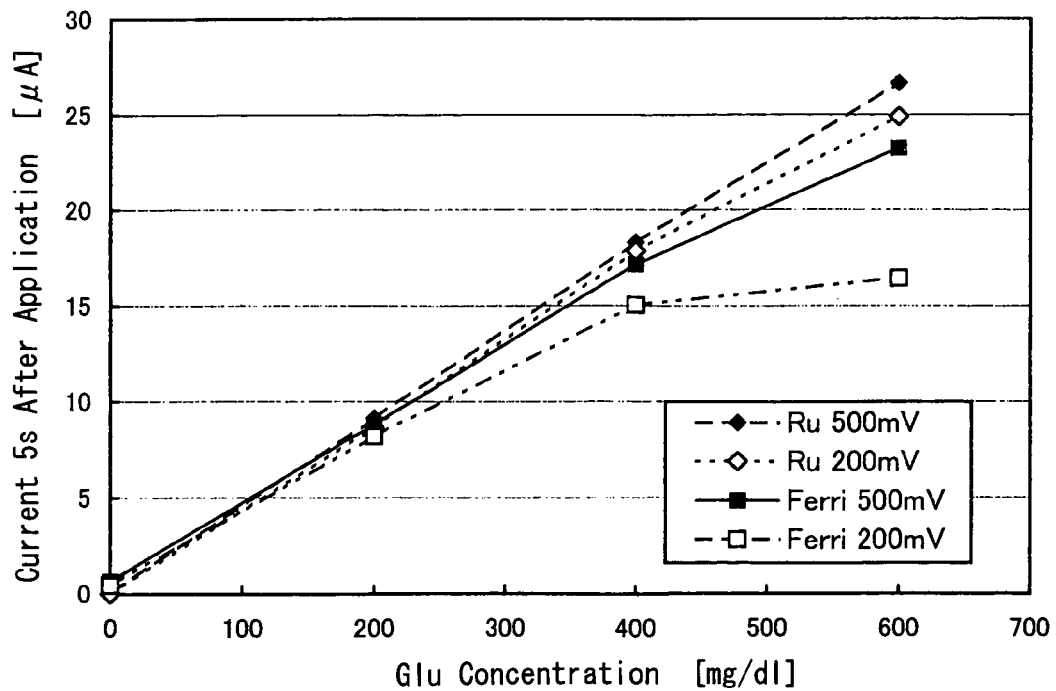
FIG. 7 is a graph of the effect of applied voltage value.

As can be seen from FIG. 7, when the applied voltage was 500 mV, the glucose sensor 1 of the present invention exhibited good linearity for the group of plotted points, indicating that glucose sensor can be measured favorably even when the glucose concentration is high (400 mg/dL or higher). In contrast, with the comparative glucose sensor 1, linearity was somewhat off when the glucose concentration was high (400 mg/dL or higher), although the overall linearity was excellent.

Meanwhile, when the applied voltage was 200 mV, the linearity of the glucose sensor 1 of the present invention was off somewhat when the glucose concentration was high (400 mg/dL or higher), but the group of plotted points did exhibit good linearity. The deviation in linearity at 200 mV with the glucose sensor 1 of the present invention was still smaller than that of the comparative glucose sensor 1 at 500 mV.

Thus, it was confirmed that when a Ru complex was used as the mediator, glucose concentration could be measured favorably within a range of glucose concentration of at least 0 to 600 mg/dL even at a low potential (applied voltage of 200 mV). Therefore, it can be concluded that the use of a Ru complex as the mediator makes it possible to drive the concentration measuring apparatus at low voltage, which lowers power consumption and reduces running costs.

Example 3

In this example, it was examined how long it took to measure the glucose concentration favorably. To this end, 500 mV voltage application between the first and second electrodes was commenced 0, 1, 2, or 10 seconds after the spot application of 1 μL of whole blood with a glucose concentration of 400 mg/dL to the reagent layer, the response current was measured during sustained voltage application, and the change over time was measured. These results are given in FIGS. 8 and 9.

Figure 8:
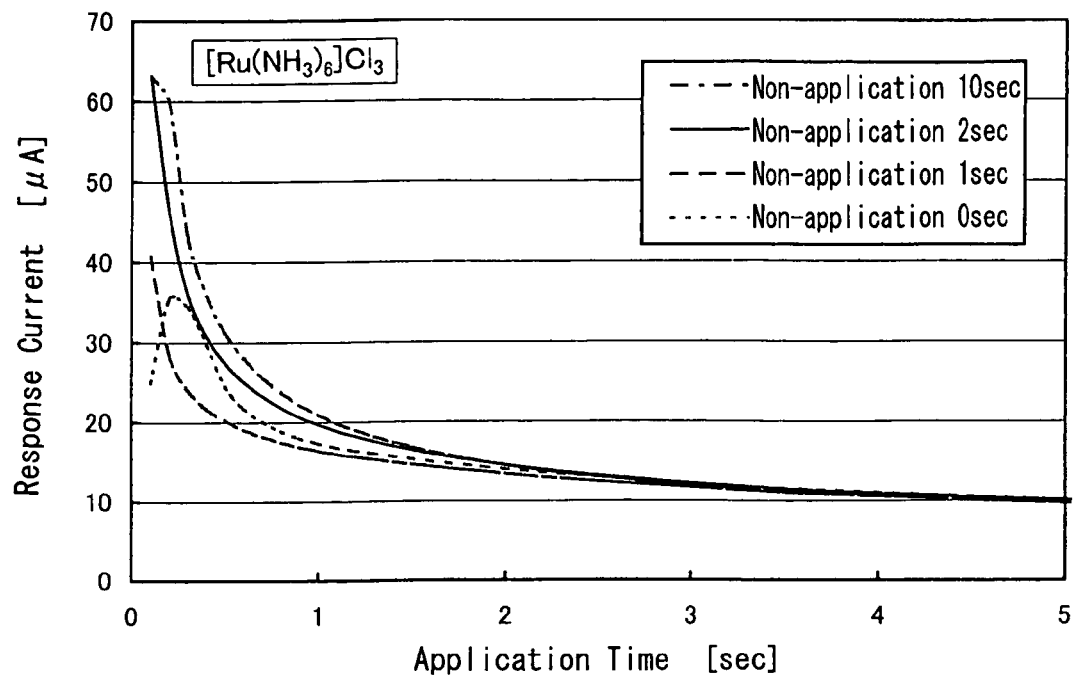
FIG. 8 is a graph of the change over time in the response current when voltage is applied to the reagent layer (closed circuit) after the circuit has been open for a specific time period after the supply of whole blood to a reagent layer in which a Ru complex is used.
Figure 9:
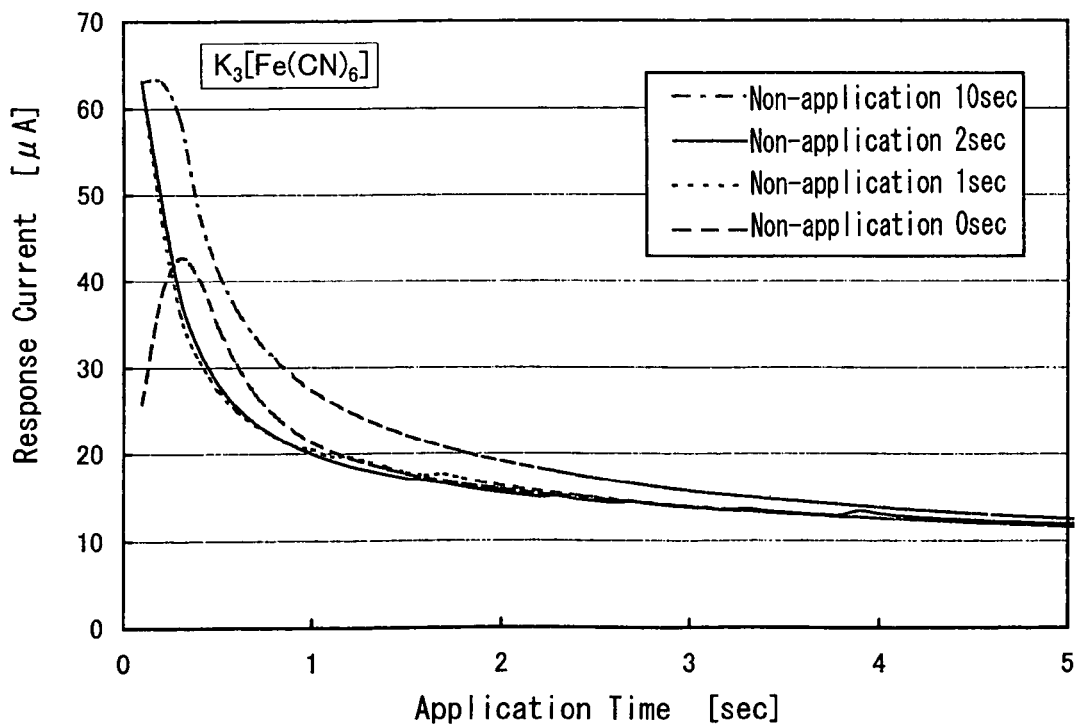
FIG. 9 is a graph of the change over time in the response current when voltage is applied to the reagent layer (closed circuit) after the circuit has been open for a specific time period after the supply of whole blood to a reagent layer in which an Fe complex is used.

It can be seen from FIG. 8 that with the glucose sensor 1 of the present invention, the individual measurement values obtained 3 seconds after the start of voltage application were the same, regardless of the time before voltage application (the time in a non-application state). Therefore, it can be concluded that the glucose sensor of the present invention gives stable measurement results as long as the application time is at least 3 seconds, and, as seen in FIG. 9, that the application time can be shorter than when an Fe complex is used as the mediator. Also, since there is no real advantage to excessively increasing the time of the non-application state, and with the results of FIG. 8 in mind, it can be concluded that 10 seconds or less is an adequate time in a non-application state with the glucose sensor of the present invention, and that 10 to 15 seconds is sufficient for the time from the glucose solution supply until the response current is measured for the purpose of computing the glucose concentration. Therefore, it can be seen from the results shown in FIGS. 8 and 9 that when a Ru complex is used as the mediator, the measurement does not take as long as when an Fe complex is used.

Example 4

In this example, the effect of reductive concomitants (the effect of background current) was examined. The response current value was measured using four different types of whole blood (with components other than glucose adjusted to their average concentration in human blood) with glucose concentrations of 0 mg/dL, 200 mg/dL, 400 mg/dL and 600 mg/dL, and using the glucose sensor 1 of the present invention and the comparative glucose sensor 1, at applied voltages of 500 mV and 250 mV. There was a voltage non-application state lasting 10 seconds after the spot application of 1 μL of whole blood to the reagent layer, after which the response current value was measured 5 seconds after the start of voltage application between the first and second electrodes. These results are given in FIGS. 10 and 11.

Figure 10:
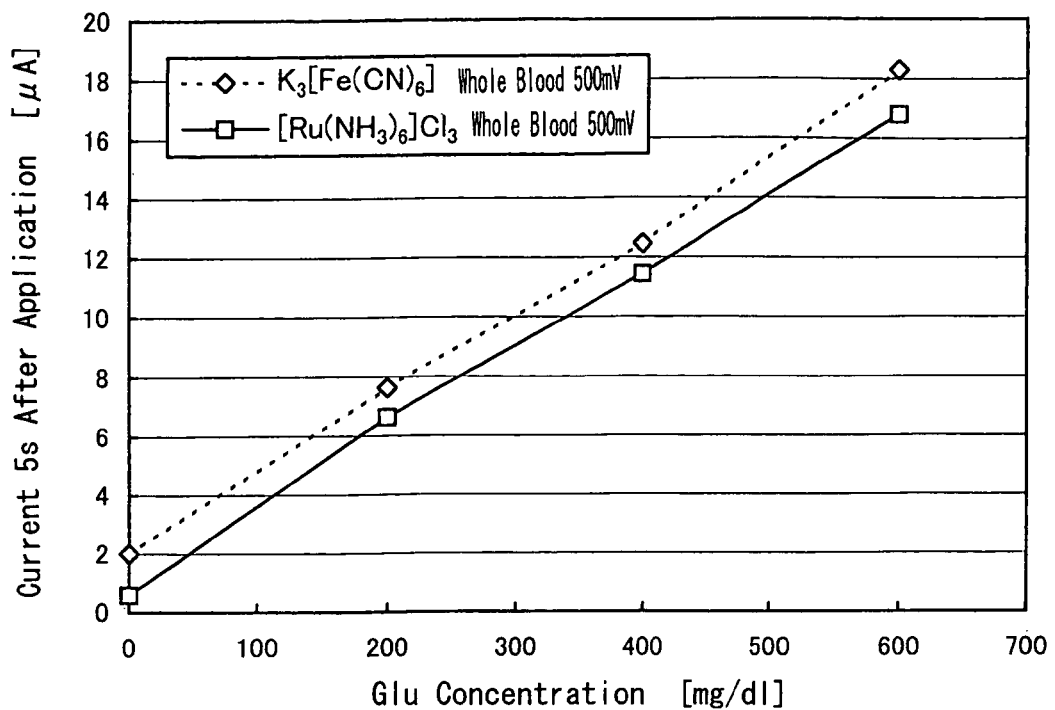
FIG. 10 is a graph of the response current value 5 seconds after the start of voltage application when a voltage of 500 mV is applied 10 seconds after whole blood is supplied to the reagent layer, for several types of whole blood with different glucose concentrations.
Figure 11:
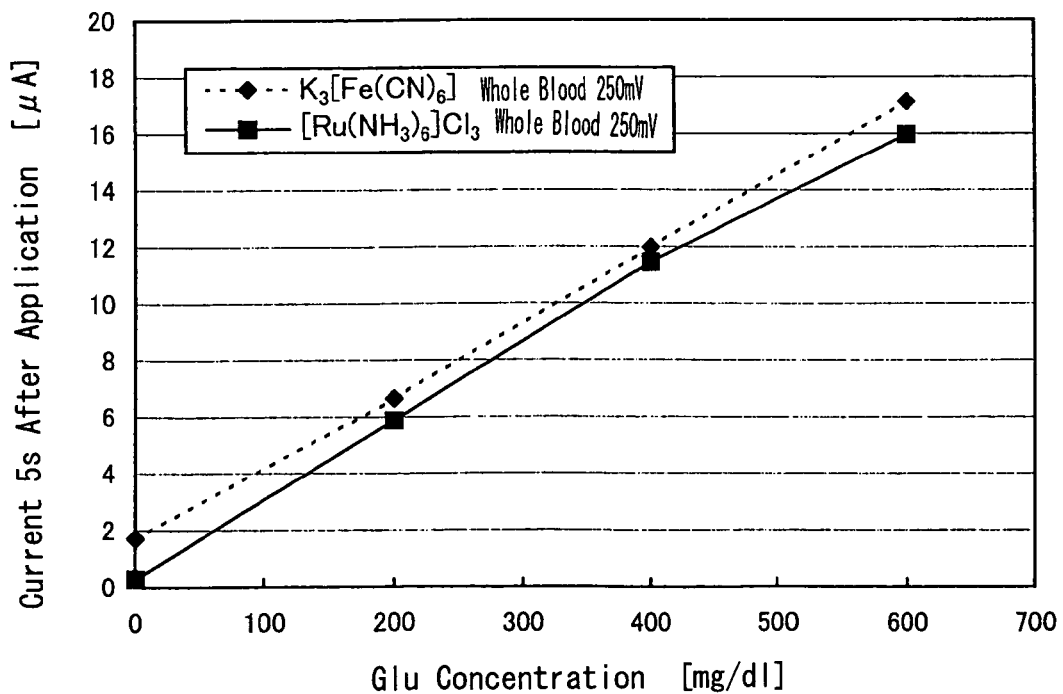
FIG. 11 is a graph of the response current value 5 seconds after the start of voltage application when a voltage of 250 mV is applied 10 seconds after whole blood is supplied to the reagent layer, for several types of whole blood with different glucose concentrations.

As can be seen from FIGS. 10 and 11, the overall response current value was higher with the comparative glucose sensor 1 than with the glucose sensor 1 of the present invention. The reason for this seems to be that the comparative glucose sensor 1 is affected more by reductive concomitants in blood than is the glucose sensor 1 of the present invention, and that the background current from these substances raises the response current value.

It should be noted here that with the comparative glucose sensor 1, the response current is measured as a positive value even when the glucose concentration is 0 mg/dL. Here again, the effect of background current caused by reductive concomitants is suspected to be the reason for the higher response current value with the comparative glucose sensor 1.

Figure 12:
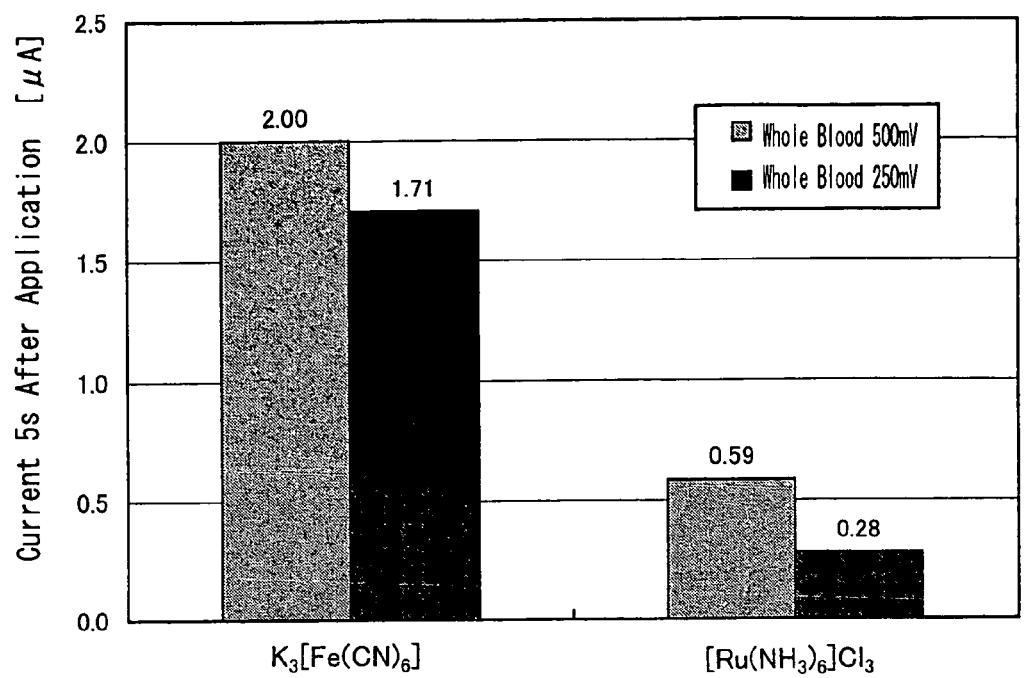
FIG. 12 is a bar graph of the response current value (background current) for whole blood with a glucose concentration of 0 in the graphs shown in FIGS. 10 and 11, given separately for an Fe complex and a Ru complex.

FIG. 12 is a bar graph of the response current value here when the glucose concentration was 0 mg/dL. It can be seen from this graph that with the comparative glucose sensor 1, a relatively large response current is measured even at a glucose concentration of 0 mg/dL, the reason for which is believed to be the greater effect of the reductive concomitants. In contrast, with the glucose sensor 1 of the present invention, the measured response current is small at a glucose concentration of 0 mg/dL, and it can be concluded that the effect of the reductive concomitants has been greatly reduced. Therefore, if a Ru complex is used as the mediator, concentration can be computed with good precision even without correcting for the effect of other reductive substances.

Example 5

Exposure resistance was evaluated in this example. This resistance to exposure was evaluated by leaving the glucose sensor 1 of the present invention and the comparative glucose sensor 1, which had both been produced at about the same time, in a thermo-hygro-static room kept at a relative humidity of 50% and a temperature of 25° C., and then using a standard solution with a glucose concentration of 0 mg/dL to measure the response current value. The application of voltage of 500 mV between the electrodes was started 10 seconds after the spot application of the standard solution to the reagent layer, and the response current value was measured 5 seconds after the start of voltage application. The glucose sensors were left 1 and 4 days inside the thermohygrostatic room. The response current value was measured under the same conditions both for a glucose sensor that had yet to be left in the thermohygrostatic room (initial), and for a glucose sensor that had been sealed in a desiccator (interior volume of 0.2 L, initial relative humidity setting of 50%, and temperature of 25° C.) containing 6 g of molecular sieve (desiccant) and then left for 4 days in a thermohygrostatic room kept at a relative humidity of 50% and a temperature of 25° C. (sealed 4 days). These results are given in FIG. 13.

Figure 13:
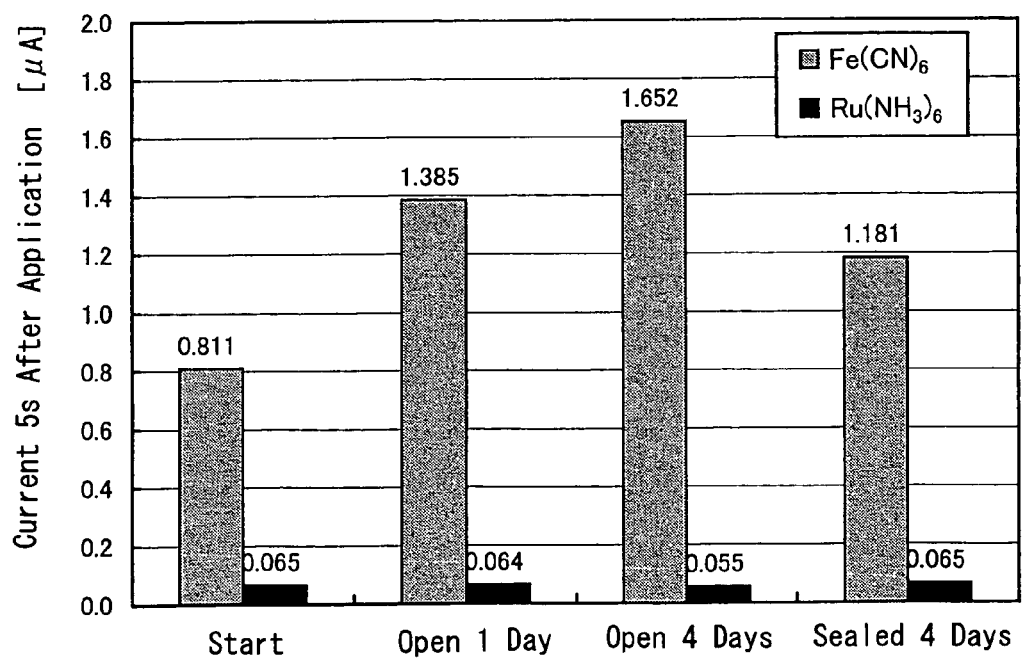
FIG. 13 is a graph of an evaluation of the effect of exposure to moisture from the response current value when a standard solution is supplied to the reagent layer.

As can be seen from FIG. 13, at all environmental settings, the glucose sensor 1 of the present invention had much smaller response current than the comparative glucose sensor 1, and the values thereof were about the same at all environmental settings. It is therefore surmised that when a Ru complex is used as the mediator, there is less degradation (reduction) of the reagent layer under the exposure environment, so storage stability is superior and long-term degradation is less likely to occur. Therefore, if a Ru complex is used as the mediator, there is no need to give much thought to the effect of exposure to moisture in the storage of the glucose sensor. This means that when glucose sensors are mass-produced and packaged on an industrial scale, there is no need to perform nitrogen replacement or other such treatment inside the packaging, which facilitates manufacture and reduces costs.

Example 6

Figure 14:
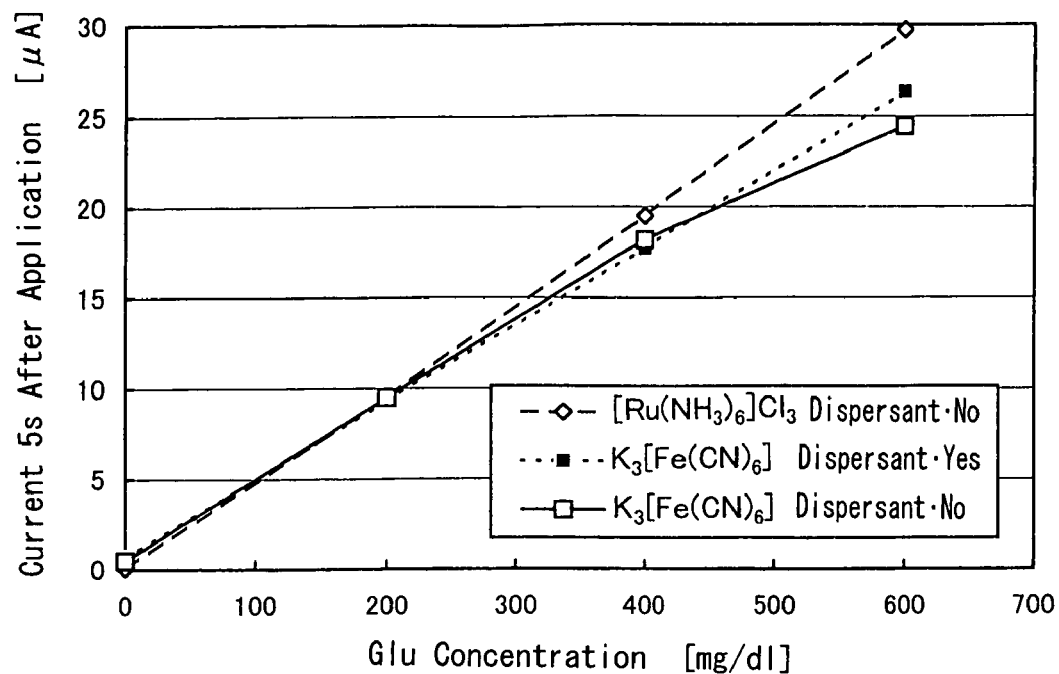
FIG. 14 is a graph of an evaluation of the dispersibility of a Ru complex from the response current value when a standard solution is supplied to the reagent layer.

The solubility of the reagent layer was examined in this example. In the examination of the solubility of the reagent layer, the response current value was measured using four different types of standard solution with glucose concentrations of 0 mg/dL, 200 mg/dL, 400 mg/dL, and 600 mg/dL and using the glucose sensor 1 of the present invention and the comparative glucose sensor 1, at an applied voltage of 500 mV. There was a voltage non-application state lasting 10 seconds after the spot application of 1 μL of standard solution to the reagent layer, after which the response current value was measured 5 seconds after the start of voltage application between the first and second electrodes. These results are given in FIG. 14. FIG. 14 also shows the results for when an inorganic gel (used as a dispersant) was added in an amount of 1 weight part per 100 weight parts Fe complex in the comparative glucose sensor 1.

As can be seen from FIG. 14, the glucose sensor 1 of the present invention exhibited excellent linearity even at a high glucose concentration. This means that the reagent layer dissolves well within 15 seconds of the supply of the standard solution, regardless of the glucose concentration.

Therefore, if a Ru complex is used as the mediator, the reagent layer will have excellent solubility, with the entire reagent layer forming a uniform reaction system, and as a result glucose concentrations can be measured in a short time and with good precision even with glucose solutions having a relatively high glucose concentration, without having to resort to the use of a dispersant or the like.

Example 7

Figure 15:
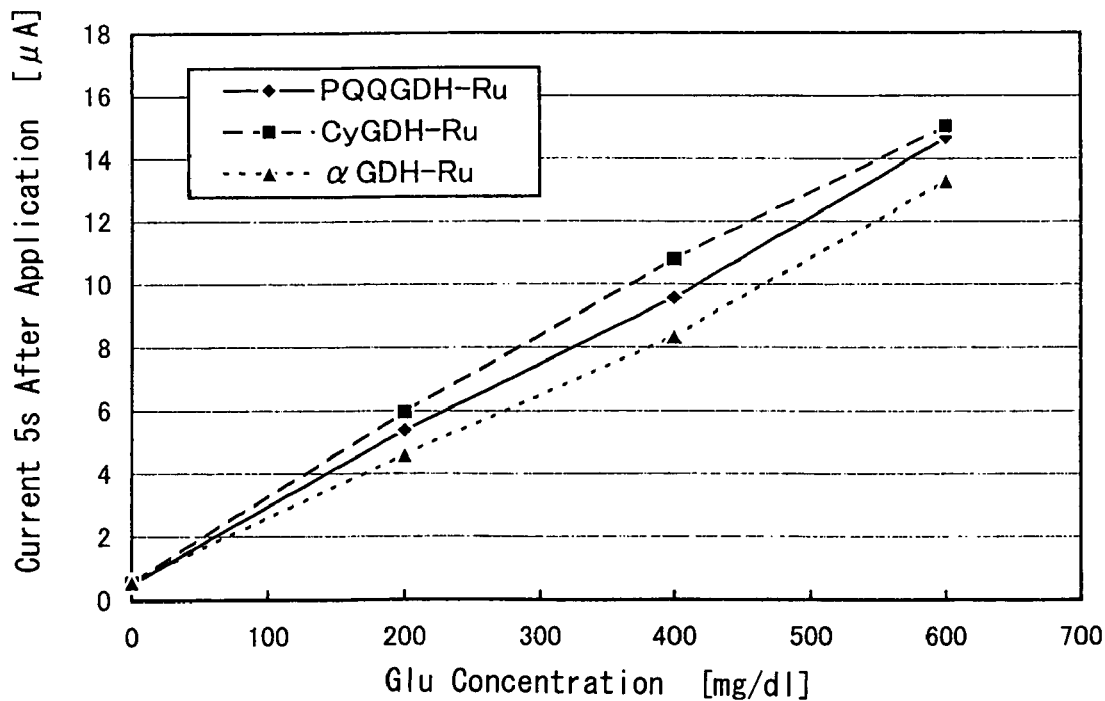
FIG. 15 is a graph of the correlation between glucose concentration and response current value for glucose sensors having different reagent layer formulations (oxidation-reduction enzymes)

In this example, the response current value was measured for the glucose sensors 2 and 3 of the present invention, which had a reagent layer formed as shown in Table 2 above, using four types of whole blood with different glucose concentrations of 0 mg/dL, 200 mg/dL, 400 mg/dL, and 600 mg/dL. These results are given in FIG. 15. FIG. 15 also shows the results for when the response current value was measured under the same conditions for the glucose sensor 1 of the present invention constituted as in Examples 1 to 6.

As can be seen from FIG. 15, with glucose sensors 2 and 3 of the present invention, in which CyGDH or a GDH was used as the redox enzyme, concentration can be measured favorably from relatively low concentrations all the way up to high concentrations, under the application of a current of just 200 mV and only a short time of 5 seconds after the start of application. FIG. 15 also tells us that the background current is small with these glucose sensors. Therefore, by using a ruthenium complex as the mediator, the advantages described in Examples 1 to 6 can be achieved for various types of GDH.

Example 8

In this example, the response current value was measured in the same manner as in Example 7 for a glucose sensor 4 of the present invention, in which a Ru complex was used as the mediator and GOD was used as the oxidation-reduction enzyme, and a comparative glucose sensor 2, in which potassium ferricyanide was used as the mediator and GOD was used as the oxidation-reduction enzyme. These results are given in FIG. 16.

Figure 16:
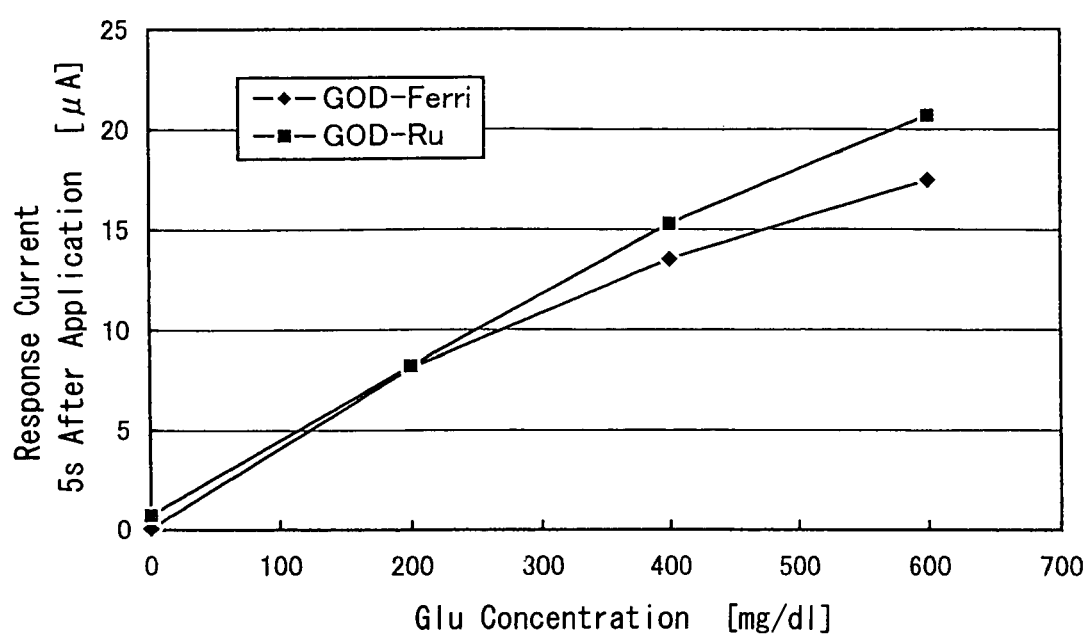
FIG. 16 is a graph of the correlation between glucose concentration and response current value for glucose sensors in which GOD is used as the oxidation-reduction enzyme.

As can be seen from FIG. 16, when GOD and a Ru complex are combined, just as with the glucose sensor 1 of the present invention used in Examples 1 to 6, linearity was excellent and background current was small even when the glucose concentration was relatively high. It can therefore be concluded that the advantages described in Examples 1 to 6 can also be achieved when GOD and a Ru complex are combined.

As described above, with the present invention, the concentration of a test target in a sample liquid can be accurately measured, whether the concentration of the test target in the sample liquid is relatively low or relatively high, the measurement will be affected less by the coexistent reductive substances present in the sample liquid, and adequate solubility of the reagent layer can be ensured.

The invention claimed is:
1. A method for measuring a concentration of a test target, the method comprising:
constructing a reaction system by supplying the test target to a reagent layer containing an oxidation-reduction enzyme and an electron mediator; measuring the concentration of the test target by utilizing;

wherein the test target is glucose, the oxidation-reduction enzyme is CyGDH, and a Ru compound is used as the electron mediator, the method further comprising:

applying constant voltage to the reagent layer; and computing the concentration of the test target on the basis of a response current value from the reagent layer;

wherein the constant voltage is no greater than 300 mV and selected from a range from a standard oxidation-reduction potential (versus a standard hydrogen electrode) between an oxidant and a reductant of the Ru compound through a standard oxidation-reduction potential (versus a standard hydrogen electrode) between ferrocyanide ions and ferricyanide ions.

2. The method according to claim 1, wherein the Ru compound is oxidative Ru(III) complex expressed by the following chemical formula:

$$[Ru(NH_3)_5X]^{n+}$$

(where X in the formula is $NH_3$ or a halogen ion, and n+ in the formula is the valence of the oxidative Ru(III) complex as determined by a type of X).

* * * * *